United States Patent [19]

Gay et al.

[11] 4,141,975

[45] Feb. 27, 1979

[54] EQUINE PARASITICIDE PASTE

[75] Inventors: John C. Gay, St. Joseph, Mo.; William P. Marsland, Spring Hill, Kans.

[73] Assignee: Cutter Laboratories, Inc., Berkeley, Calif.

[21] Appl. No.: 848,257

[22] Filed: Nov. 3, 1977

[51] Int. Cl.$^2$ ............................................. A61K 31/66
[52] U.S. Cl. ................................................. 424/217
[58] Field of Search ........................................ 424/217

[56] References Cited

U.S. PATENT DOCUMENTS 3,070,489  12/1962  Newallis .............................. 424/217

OTHER PUBLICATIONS

Chervyakov et al.–Chem. Abst.–vol. 73, (1970), p. 123532q.
Dodek et al.–Chem. Abst., vol. 67, (1967), p. 90,008u.
Koishibaev et al.–Chem. Abst., vol. 75, (1971), p. 109,114q.

Primary Examiner—Sam Rosen
Attorney, Agent, or Firm—Bertram Bradley; Robert E. Allen; James A. Giblin

[57] ABSTRACT

Semi-solid preparation useful as a boticide and anthelmintic in horses and comprising an effective amount of trichlorfon dispersed in a mineral oil.

9 Claims, 1 Drawing Figure

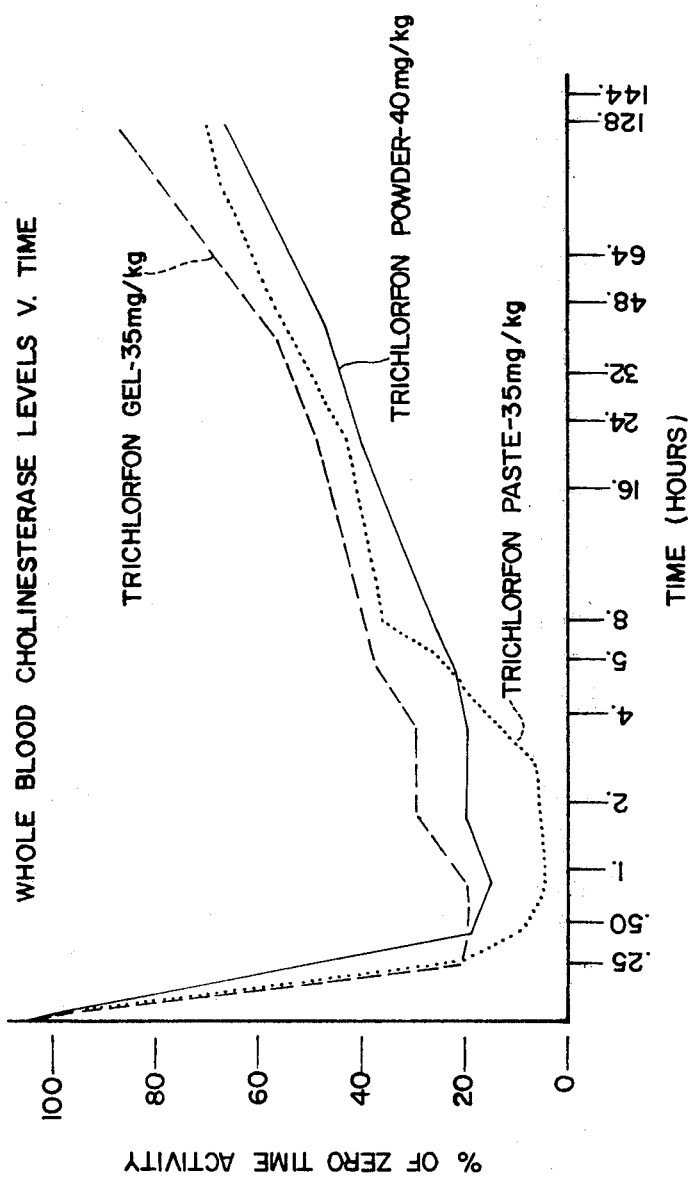

EQUINE PARASITICIDE PASTE

BACKGROUND OF THE INVENTION

1. Field

This disclosure is concerned generally with compositions useful for controlling endoparasites in horses and specifically with a paste-like preparation of trichlorfon which demonstrates a high degree of stability and bioavailability.

2. Prior Art

Trichlorfon (O,O-Dimethyl-1-hydroxy-2,2,2-trichloroethylphosphonate) is a well known and proven anthelmintic and boticide in the horse. The compound is described in U.S. Pat. No. 2,701,255 to Lorenz. Trichlorfon is commonly available commercially in a dry form (e.g. Anthon ® horse anthelmintic) from which a liquid formulation can be readily prepared. Unfortunately, the shelf life of available forms of trichlorfon is limited and it is known that presently available trichlorfon will degrade with time. Also, presently available forms of trichlorfon limit its bioavailability over prolonged periods of time.

Although other equine parasiticidal preparations in paste form have been disclosed (i.e. U.S. Pat. No. 3,746,490 to Marsland et al disclosing a resin-based paste formulation of the liquid dimethyl-2,2-dichlorovinyl phosphate or DDVP), we are unaware of any prior disclosure of a trichlorfon paste. We have prepared a paste-like formulation of trichlorfon which not only appears to have an infinite shelf life under normal storage conditions of 25°–30° C. but, quite surprisingly, a higher degree of bioavailability at lower dosage rates than other forms of the same compound. Details of our formulation are described herein.

SUMMARY OF THE INVENTION

Our stable, highly bioavailable equine boticide and anthelmintic paste-like preparation comprises a boticidally and anthelmintically effective amount of trichlorfon dispersed in an inert mineral oil carrier. In preferred embodiments, the preparation comprises a composition including about 5 to 70 weight % trichlorfon dispersed in about 30 to about 70 weight % mineral oil. Thickening agents such as colloidal silica ranging in amount from 0 to 40 weight % may be included to assure an acceptable paste-like consistency when lighter mineral oils are used. Flavoring or sweetening agents ranging from about 0 weight % to about 20 weight % may be added to enhance palatability. Unlike the DDVP Paste cited above, our paste does not require the use of resin particles to achieve a paste-like texture.

SPECIFIC EMBODIMENTS

For reasons disclosed in greater detail in U.S. Pat. No. 3,746,490, cited above, our information should be in a paste-like form. In general, that form permits the introduction (e.g., via syringe) of the active agent directly into the mouth of the horse. This results in a significant portion of the paste adhering to the palate and inner portions of the mouth thereby resulting in destruction of first instar bot larvae in contact with the active agent. In time, the active agent is swallowed and introduced into the stomach and intestine to result in both direct contact killing and systemic killing of 1st, 2nd and 3rd instar bot larvae and several species of endoparasitic worms in the horse.

It should be stressed that our paste formulation requires that a mineral oil be used as the inert carrier, preferrably about 30 to 70 weight %. As used herein, the expression mineral oil includes all aliphatic hydrocarbons of mineral origin which, when used alone or with inert thickening agents, and subsequently blended with an effective amount of trichlorfon, will result in a preparation having the consistency of a paste. Paste refers to a soft, semi-solid material consisting of a fluid medium that contains an insoluble solid dispersed phase. Ideally, the paste is tacky and readily adheres to a horse's teeth and hard palate and is physically insensitive to minor temperature variations.

A mineral oil is preferred over vegetable oils to avoid rancidity with time, to reduce hydrolysis of the trichlorfon active agent, and because it is not digested during use. It is thought that the above factors contribute to both stability and bioavailability.

Examples of mineral oils which can be used in accordance with this disclosure include liquid mineral oils and semi-solid petrolatum having aliphatic chains of 16 to 60 carbon atoms. Such mineral oils include conventional liquid mineral oils as well as semi-solid petrolatum. In the case where liquid mineral oil is used (e.g. mineral oil, U.S.P.) conventional inert fillers such as colloidal silica, resins, natural and synthetic clays, and cellulose derivatives may be used to assure an acceptable consistency.

The trichlorfon is preferably added to the mineral oil in granular or powder form, milled to a particle size range of about 1 to 1000 microns preferably about 1 to 100 microns.

The preparation of a specific preferred formulation is described below. That formulation was used in the animal studies which are also described below.

EXAMPLE

Our preferred formulation was prepared from a concentrate consisting of 82.0 wt. % of trichlorfon (technical grade 100) in granular form and 18 wt. % colloidal silica (Hi-Sil ® 233). The trichlorfon and colloidal silica were combined, mixed well, and milled (to a particle size range of about 1 to 100 microns).

The paste was prepared by adding a small amount of brown sugar flavoring to the mineral oil and mixing well until all agglomerates were well dispersed. The trichlorfon concentrate was then added and mixed with the oil until homogeneous. The final paste was then filled and stored in 32 cc syringes.

The final paste included the following ingredients:

TABLE I

| Ingredient | % w/w |
| --- | --- |
| trichlorfon concentrate | 50.0* |
| brown sugar flavor | 0.5 |
| mineral oil | 49.5 |

*this provided 40% trichlorfon active ingredient in the formulation with an overage of up to 2.5% to cover manufacturing loss.

Stability Studies

The stability of the paste formulation was found to be quite superior to both the dry (ANTHON®) and a trichlorfon gel formulation. The gel consisted of 40 wt. % of trichlorfon in an alcohol gel. The shelf life of each product was calculated by linear regression. This shelf life was determined by obtaining initial values for the product as it would be when it was prepared for sale. The product was then stored in its commercial container at temperatures of −12° C., 30° C., 40° C., and 50° C. and periodically evaluated for potency. These resulting data were then taken and treated statistically to determine the acceptability of the given product. This acceptability was determined by comparing the beginning potency with that potency at which the product falls below 90% of the initial potency.

The method used to determine drug content in all three formulations was dehydrohalogenation, which is the typical method common to products containing trichlorfon as an active ingredient. Calculations show that the shelf life at 30° C. of the products are dramatically different. The table below gives that information:

TABLE II

| Shelf Life at Room Temperature (30° C) | |
|---|---|
| Preparation | Months |
| ANTHON ® Horse Wormer | 24.2 |
| Trichlorfon gel | 4.1 |
| Mineral Oil - Paste | Infinite |

The shelf life of trichlorfon paste was found to be quite unexpectedly long. As can be seen the shelf life of the paste is shown as infinite, while the other formulas indicate some loss of the drug during storage. It is clear that the paste is superior from the view point of its stability.

Bioavailability Studies

To evaluate both our paste and a gel formulation of trichlorfon it was decided to compare their bioavailabilities with a 90% trichlorfon feed additive formulation that is commercially available under the trade name of ANTHON ® horse anthelmintic. Trichlorfon kills parasites by inhibiting, within the parasite, the enzyme cholinesterase. Trichlorfon also inhibits, to a lesser degree, the cholinesterase of the mammalian host. By measuring the blood cholinesterase of horses prior to and following dosing of the various formulations of trichlorfon, it was possible to measure the relative bioavailability of trichlorfon from each of the formulations.

Fifteen registered quarter horses of similar genetic background were used, five for each formulation. This proved to be an excellant data set for statistical comparison. One of the goals of the investigation was to determine if the formulation of trichlorfon would be equivalent to the standard feed additive formulation at a slightly lower dose.

The paste and the gel were administered to the horses at 35 mg/kg and the ANTHON ® feed additive formulation at 40 mg/kg. The ANTHON ® feed additive formulation was mixed as per label directions with one gallon of grain and all 5 horses consumed the medicated feed within 15 to 30 minutes of administration. Both the paste and the gel formulations were swallowed immediately at the time of administration.

Zero time for starting the experiment was that time when the medicated feed was placed in front of each horse or when the gel or paste was placed on the tongue. Blood samples were collected for cholinesterase determinations via the jugular vein at 0, 15 and 30 minutes and at 1, 2, 4, 6, 24, 48 and 144 hours. At each interval, 5 millimeters of blood were collected in a vial containing 0.05 ml. of 10% Ethylenediamine Tetraacetic Acid (E.D.T.A.) solution. Samples were refrigerated immediately and then tested for cholinesterase activity. A modification of the method of Michel (J. Lab. And Cl. Med., Vol. 34, 1949) to adapt the method to animals were used to determine cholinesterase activity. Each horse served as its own control and the pretreatment level was used as the 100% activity level. All post-exposure samples were compared to the pretreatment sample and all are expressed as percent of zero time activity. Observations for signs of toxicity were observed and recorded if found. Observations of fecal consistency and parasite passage were also made for several days following administration of the drug. The FIGURE shows the degree of cholinesterase depression of all three formulations on whole blood cholinesterase.

Five horses are represented on each formulation and the mean enzyme activity levels with time of the horses in each group are plotted in the FIGURE. All three formulations caused rapid decreases in whole blood cholinesterase during the first half hour following administration. It should be noted that the ANTHON ® feed additive formulation is approximately 15 minutes behind the paste and gel formulations in reaching this point. This would be expected since it took up to 30 minutes for all horses to consume the complete dose of the anthelmintic administered in the feed, whereas the paste and gel were introduced into the system almost immediately at time 0. Maximum cholinesterase depression occurs with all formulations by one hour after ingestion. Those horses that received the trichlorfon gel or ANTHON ® formulation show a recovery of cholinesterase level beginning almost immediately after it reaches its low point at one hour. This recovery of cholinesterase progressively increased until at 6 days (144 hours) after exposure the cholinesterase had recovered to approximately 60% of normal for the ANTHON ® preparation and 85% for the trichlorfon gel. Trichlorfon gel and ANTHON ® preparation show very similar responses, but the gel appears to have less trichlorfon available since the depression is less and the recovery is quicker than with the ANTHON ® preparation. This would be expected, however, with approximately a 10% lesser dose of trichlorfon being administered with the gel than from the ANTHON ® preparation (35 mg/kg vs. 40 mg/kg).

The response of the trichlorfon paste is quite different and was also quite unexpected. The paste, as with both the gel and the feed additive formulation, depressed cholinesterase to its maximum effect after one hour, but unlike the gel or the ANTHON ® formulation, the paste maintained this level of depression for approximately two more hours. At three hours the horses to whom the paste has been administered showed a very rapid recovery of cholinesterase level and at the end of 6 days the recovery of cholinesterase level of the horses receiving the trichlorfon paste was slightly above those that had received ANTHON ® feed additive. Based on this data, the trichlorfon paste offers clear advantages over the trichlorfon gel. The paste had a more rapid effect, greater availability, and more rapid recovery of cholinesterase than did the ANTHON ® formulation. This, translated into practical efficacy and safety, means that one would expect the trichlorfon paste to have a slightly better efficacy than the feed additive formulation of trichlorfon and present less prolonged risk to the horse since cholinesterase levels would recover more rapidly from a therapuetic dose of the paste than from an equivalent dose of ANTHON ® feed additive. This effect is quite remarkable when one considers that the dosage of trichlorfon paste in these studies was 35 mg/kg of body weight and the ANTHON ® preparation was administered at 40 mg/kg of body weight.

Bioavailability differences between the ANTHON ® formulation and trichlorfon paste and trichlorfon gel were compared statistically using the Student t test comparing differences between two means at the 5% level. Table III represents the values and results for plasma cholinesterase. The column on the left represents the gel vs. the ANTHON ® formulation. On the right the cholinesterase level resulting from use of the paste vs. the ANTHON ® formulation is compared. Note that there were no significant differences in the depression of plasma cholinesterase between the gel formulation and the ANTHON ® formulation. It should also be noted that with the paste there were significant differences, with the paste having more available trichlorfon at 35 mg/kg than the ANTHON ® preparation had at 40 mg/kg for the first 4 hours after the administration and no significant difference from then on.

TABLE III t-Test Comparison of the Three Different Formulations of Trichlorfon
PLASMA CHLINESTERASE

| Sample Time | Gel vs. Anthon ® Formulation | Anthon ® Formulation vs. Paste |
|---|---|---|
| 15 minutes | N.S. | Significant |
| 30 minutes | N.S. | Significant |
| 1 hour | N.S. | Significant |
| 2 hours | N.S. | Significant |
| 4 hours | N.S. | Significant |
| 6-8 hours | N.S. | N.S. |
| 24 hours | N.S. | N.S. |
| 48 hours | N.S. | N.S. |
| 144 hours | N.S. | N.S. |

It should be noted that the depression of circulating blood cholinesterase is not an indication of intoxication by a cholinesterase inhibiting substance. There are cholinesterase inhibiting substances that are known to produce death prior to depression or circulating blood cholinesterase. On the other hand, compounds like trichlorfon may depress circulating cholinesterase 100% and the animal not show any signs of clinical intoxication. Depression of whole blood or plasma cholinesterase is only an indication of exposure to a cholinesterase inhibiting substance. Toxic signs from cholinesterase inhibiting substances may be substantiated by measurement of brain cholinesterase, not circulating cholinesterase. Unfortunately, it is extremely difficult if not impossible to measure brain cholinesterase in a live animal. Therefore, circulating blood cholinesterase should only be used as an indication of exposure to cholinesterase inhibiting substances and not the level of intoxication.

Parasitidal Studies

Table IV summarizes the parasiticidal performance of the trichlorfon paste at 35 mg/kg in tests done with 10 horses (two separate locations, five horses in each location). The number in parentheses is the number of parasites removed over the number of parasites remaining at necropsy. As can be seen from Table IV both boticidal and anthelmintic efficacy was achieved with the paste formulation.

TABLE IV

Parasitidal Results with Trichlorfon Paste at 35 mg/kg

| Location | No. Horses Examined | Percent Efficacy | | | |
|---|---|---|---|---|---|
| | | Bots | | Ascarids P.equorum | Pinworms O.equit |
| | | G. intestinalis | G.nasalis | | |
| Texas | 5 | (313/2) 99.4% | (195/0) 100% | (95/0) 100% | (325/0) 100% |
| Kansas | 5 | (237/1) 99.6% | (24/0) 100% | (10/0) 100% | (30/0) 100% |

In other work, at conventional trichlorfon doses of 40 mg/kg, the trichlorfon paste was tested against experimental first instar infections of *Gasterophilus intestinalis* and *Gasterophilus nasalis*. This work is reported by Drudge et al, "Critical and Controlled Tests of Antiparasitic Activity of Liquid and Paste Formulations of Trichlorfon in the Horse", Vet. Med. & Sm. An. Cl., Aug. 1975. These results revealed 100% effectiveness against first, second and third instars *Gasterophilus intestinalis* and *Gasterophilus nasalis, Parascaris equorum* and *Oxyuris equi* at 40 mg/kg and 100% efficacy against the first instars of both *G. intestinalis* and *G. nasalis* at 20 and 17.5 mg/kg of body weight.

Safety and Clinical Studies

The safety of the trichlorfon paste formulation was tested and confirmed in clinical trials in 14 locations across the United States. The clinical studies are described in detail in a paper presented by W. P. Marsland et al. at the July 11-16, 1977 meeting of the World Assoc. for Advancement of Veterinary Parasitology, Sidney, Australia.

Given the above disclosure, it is thought that the above paste formulation is subject to numerous variations which will occur to those skilled in the art. Accordingly, it is intended that the above example should be construed as illustrative and that the scope of the invention should be limited only by the following claims.

We claim:

1. An equine parasiticide paste comprising a boticidally and anthelmintically effective amount of particles of trichlorfon dispersed in an inert mineral oil carrier, the composition having a paste-like consistency such that, when introduced into the mouth of a horse, at least a portion of the composition is adapted to adhere to the palate and inner portions of the mouth of the horse.

2. The composition, as claimed in claim 1, wherein the amount of trichlorfon ranges from about 5 to 70 wt. %.

3. The composition, as claimed in claim 1, wherein the amount of mineral oil carrier ranges from about 30 to 70 wt. %.

4. The composition, as claimed in claim 1, wherein the mineral oil carrier is thickened with an inert filler to achieve a paste-like consistency.

5. The composition, as claimed in claim 4, wherein the filler is colloidal silica.

6. The composition, as claimed in claim 1, wherein the mineral oil is petrolatum.

7. The composition, as claimed in claim 1, wherein up to 20 wt. % of a flavoring agent is included in the composition.

8. The composition, as claimed in claim 1, wherein the amount of trichlorfon ranges from about 5 to 70 wt. %, the amount of mineral oil ranges from about 30 to 70 wt. %, and the mineral oil includes an inert filler material in an amount sufficient to assure a paste-like consistency in the composition.

9. The composition, as claimed in claim 8, wherein the trichlorfon particles has an average particle size ranging from about 1 to 1000 microns.

* * * * *